(12) United States Patent
Freeman et al.

(10) Patent No.: US 7,030,072 B2
(45) Date of Patent: Apr. 18, 2006

(54) AERATED CLEANSER AND A METHOD OF DISPENSING THE SAME

(75) Inventors: Faith Freeman, Huntington Beach, CA (US); Scott H. Freeman, Huntington Beach, CA (US); Frank H. Asbury, Anaheim, CA (US)

(73) Assignee: Primal Elements, Inc., Garden Grove, CA (US)

( * ) Notice: Subject to any disclaimer, the term of this patent is extended or adjusted under 35 U.S.C. 154(b) by 55 days.

(21) Appl. No.: 10/894,530

(22) Filed: Jul. 20, 2004

(65) Prior Publication Data

US 2005/0090413 A1 Apr. 28, 2005

Related U.S. Application Data

(63) Continuation-in-part of application No. 10/694,545, filed on Oct. 27, 2003.

(51) Int. Cl.
*A61K 7/00* (2006.01)
(52) U.S. Cl. .................. 510/130; 510/137; 510/424; 510/426; 510/428; 510/505; 424/70.1
(58) Field of Classification Search .................. None
See application file for complete search history.

(56) References Cited

OTHER PUBLICATIONS

Website, www.dove.com; Dove Beauty Bars with unique one-fourth moisturizing lotion. (2 pages).
Website, www.suncitysoap.com; "Commercial Soap Manufacturing". (4 pages).
Website, www.cleaning101.com; "Manufacturing" 5 page article about soap manufacturing.

*Primary Examiner*—Necholus Ogden
(74) *Attorney, Agent, or Firm*—Stetina Brunda Garred & Brucker

(57) ABSTRACT

A cleanser is provided comprising a glycerin based mixture which may have been aerated. The aerated mixture may be combined with a selected fragrance and a selected colorant. The selected fragrance and colorant may correspond to a food product such as a vegetable, fruit, ice cream or the like. Moreover, first and second aerated mixtures may be extruded out of a funnel simultaneously into a rotating container to impart a swirl configuration on the mixtures filling the container. The aerated cleanser may be combined with real food products such as vegetable and fruits. Lastly, the aerated cleanser of the present invention may be formed into a scooped ice cream shape by scooping the same with an ice cream scoop.

10 Claims, 4 Drawing Sheets

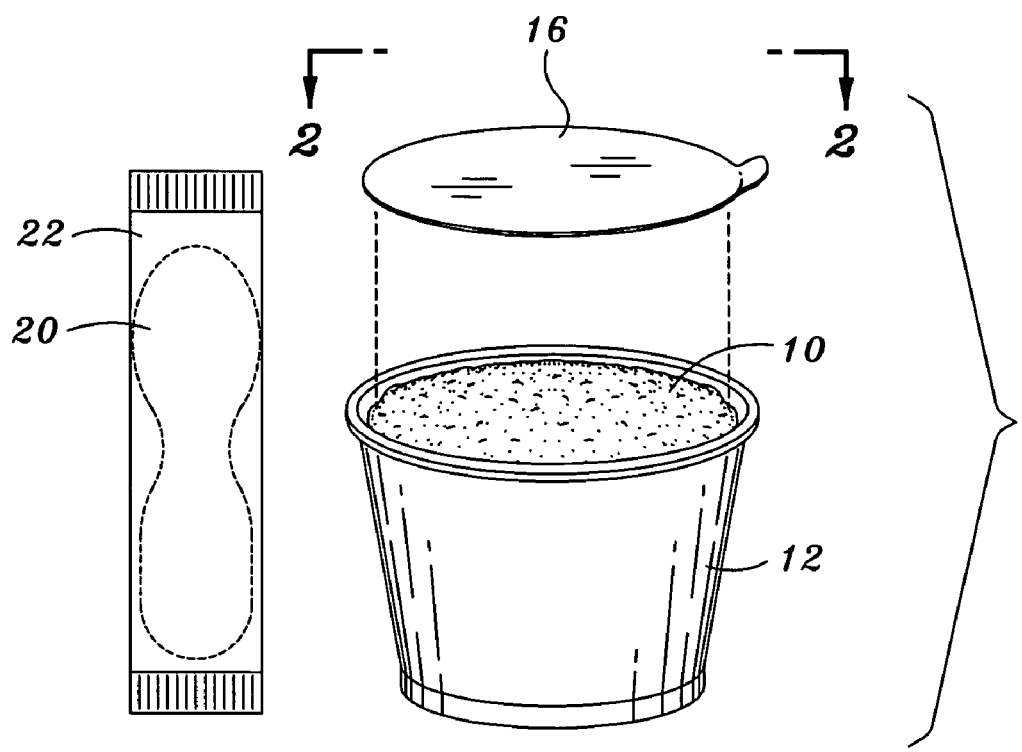
Fig. 1
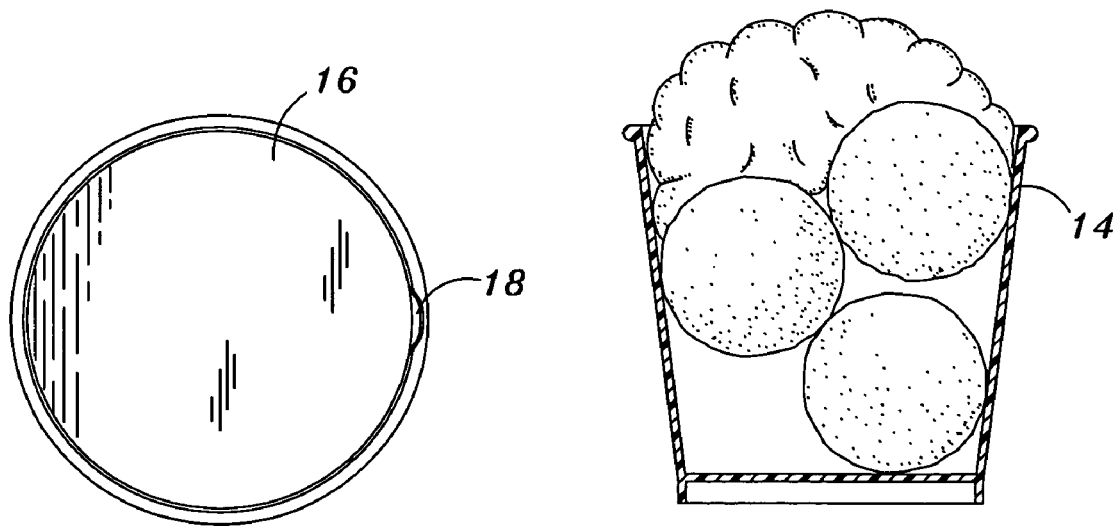
Fig. 2
Fig. 3

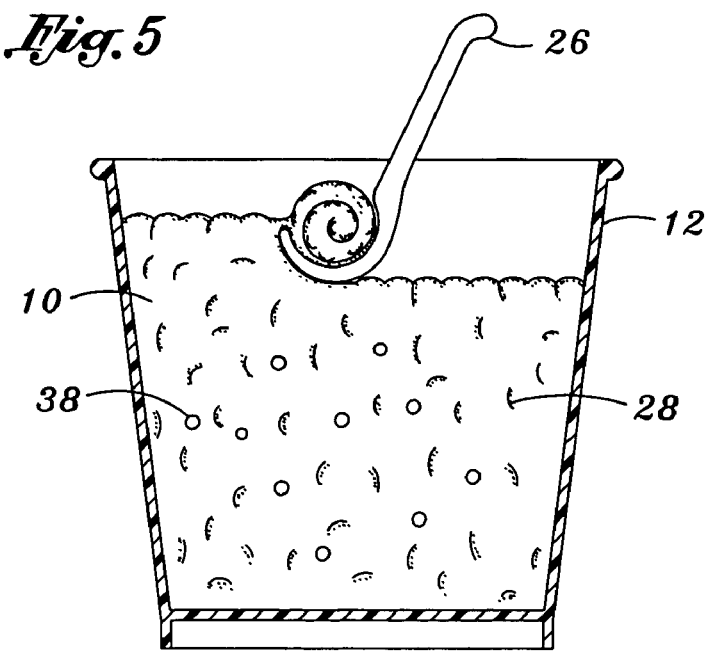
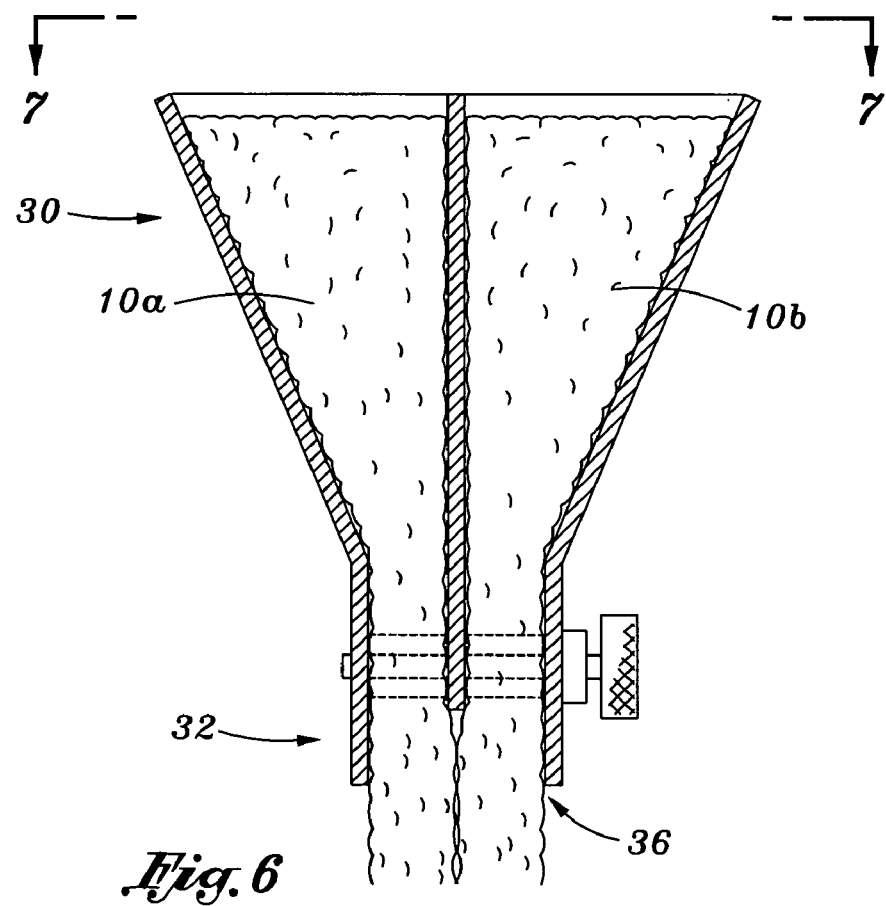

AERATED CLEANSER AND A METHOD OF DISPENSING THE SAME

CROSS-REFERENCE TO RELATED APPLICATIONS

This is a continuation in part of application Ser. No. 10/694,545, filed Oct. 27, 2003 now pending the contents of which are incorporated herein by reference.

STATEMENT RE: FEDERALLY SPONSORED RESEARCH/DEVELOPMENT

Not Applicable

BACKGROUND OF THE INVENTION

The present invention relates generally to a cleanser, and more particularly to an aerated cleanser with selective fragrances and colorants combined with the aerated cleanser, a plurality of aerated cleansers filled within a container having a swirl configuration, an aerated cleanser combined with real food products, an aerated cleanser formable into a scooped ice cream shape, and a method of dispensing the same.

Skin cleansers are routinely utilized to clean portions of a human body such as the hands, feet and face. Cleansers may be modified to make the same easier to use and more attractive compared to the actual cleanser base or raw material. For example, cleansers may include various fragrances or coloring to be more aesthetically pleasing to the user. Cleansers may also be packaged in various configurations to make distribution of the cleanser to retail stores and consumers simpler and more efficient. This may be accomplished by individually packaging the cleansers as solid bars with a plastic or paper outer covering. In the alternative, cleansers may be formed as a semi-viscous fluids such that the cleansers may be dispensed out of a pump bottle by consumers.

The present invention provides alternative embodiments with respect to cleansers to make the same even more attractive to consumers in relation to their visual appearance such as its color and texture, feel, and aroma. Additionally, the present invention provides alternative embodiments with respect to the method of dispensing such cleansers.

BRIEF SUMMARY OF THE INVENTION

In accordance with the present invention, there is provided a detergent/cleanser preferably comprising a glycerin based cleanser and preferably including a colorant. The cleanser may be formed to simulate the consistency of ice cream, sherbet or the like having similar texture, color and odor. The cleanser preferably comprises a mixture of about 10% to about 25% glycerin, about 10% to about 25% Water, about 10% to about 25% Sodium Cocoyl Isethionate, about 10% to about 25% Sorbitol, about 5% to about 10% Propylene Glycol, about 5% to about 10% Disodium Lauryl Sulfosuccinate, about 1% to about 5% Stearic Acid, about 0.5% to about 1% Sodium Chloride, up to 0.1% Pentasodium Pentate. With respect to the colorant, the same may be selected from the group consisting of Red 3 CI#45430, Blue #1 CI#42090, Yellow 5 CI#11380, Yellow 6 CI#11390, Blue #2 CI#73015, Red 40 CI#16035, and combinations thereof such that the cleanser resembles various flavors of ice cream. The detergent/cleanser may then be disposed in various size containers for shipping and ultimate display and dispensing to retail consumers. Preferably, such containers comprise half gallon, one gallon or five gallon containers which are similar in appearance to conventional ice cream containers used in the ice cream trade. Additionally, it is contemplated that various containers will be utilized, each having a different color and/or flavor cleanser therein to simulate differing ice cream and/or sherbet flavors.

The applicants have additionally discovered that the detergent/cleanser may be mechanically agitated such as in a conventional mixer wherein the same is aerated. The agitation and aeration can be utilized to aerate the cleanser to include approximately 20%–75% air therein. Preferably, the aeration is between 30%–50% air which has been found to cause the aerated cleanser to simulate the consistency and appearance of conventional whipped cream. During such agitation and aeration, suitable fragrances and/or colorants can additionally be added such that the resultant whipped cleanser additionally simulates the smell of conventional whipped cream.

In the preferred embodiment, the present invention contemplates dispensing the cleanser and/or whipped cleanser in a manner to simulate the dispensing of ice cream and whipped cream. In this regard, a hand ice cream scoop may be used to obtain a quantity of the cleanser from its storage container. The same may then be placed in a conventional cup, cone or the like. One or more scoops of cleanser may be disposed within the cup and subsequently the whipped cleanser may be disposed over the top of the cleanser disposed within the cup. By this procedure, the consumer is able to select desired fragrances and colors of the cleanser and, in effect, form a cleanser sundae for later use by the consumer.

The applicants have additionally found that the whipped cleanser can additionally be provided with granulated sugar which is retained within the whipped cleanser to serve as a natural exfoliant during the cleansing process. In the preferred embodiment, approximately 10%-50% by weight granulated sugar is mixed with the whipped cleanser. The whipped cleanser of course can be dispensed separately from the non-whipped cleanser or, alternatively, concurrently therewith.

In another aspect of the present invention, the aerated cleanser may have selected colorants and fragrances combined with the aerated cleanser. The selection of the colorants and fragrances may be in accordance with a common theme such as a food product or may be as desired by a customer. By way of example and not limitation, the aerated cleanser combined with selected colorants and fragrances may be fabricated in accordance with vanilla, chocolate, and strawberry food product. As an example, a chocolate fragrance may be combined with the aerated cleanser along with a brown colorant such that the aerated cleanser may resemble chocolate. Alternatively, the aerated cleanser may have selected colorant and fragrance added therein such that the aerated cleanser may be fabricated to resemble a desired ice cream flavor. Moreover, the aerated cleanser may be formable into a shape of scooped ice cream by scooping out the ice cream resembling aerated cleanser with an ice cream scoop.

The aerated cleanser may be combined with a first colorant and corresponding first fragrance to define a first aerated cleanser. And, a second aerated cleanser may be combined with a second colorant and a corresponding second fragrance to define a second aerated cleanser. The first and second aerated cleansers may be filled into a hopper and subsequently, simultaneously forced through a funnel and filled into a container. A swirl configuration may be imparted onto the aerated cleansers filling the container by slowly rotating the container while the container is being filled with the aerated cleansers.

The funnel may be connected to a measuring piston. The measuring piston defines two positions, namely, an open position and a closed position. The measuring piston in the closed position may be the normal position. In this closed position, the aerated cleansers remain in the hopper and fennel and do not pass through the funnel. In contrast, in the open position, the aerated cleansers flow through the fennel. It has been found that the first and second aerated cleansers even though they may pass through the funnel simultaneously remain segregated.

In another embodiment of the present invention, the aerated cleanser may be combined with food products and a method of selling the same are provided. By way of illustration and not limitation, the food products may be apples, oranges or combinations thereof. The food product may be combined with the aerated cleanser when the cleanser is being agitated or after the cleanser has been agitated.

In another embodiment of the present invention, the method of dispensing the aerated cleanser mixed with food product may comprise providing a variety of aerated cleansers made to resemble various food products, providing a variety of real food products, and combining selected aerated cleansers and selected food products which are selected by a customer. For example, the aerated cleanser(s) and food product(s) may be provided at a point of purchase location separated from each other. At the point of purchase, the customer may select an aerated cleanser and may select a food product. At this point, the selected aerated cleanser and selected food product may be combined together and sold to the customer. The food product may be selected from the group consisting of vegetables, fruit, berries, and combinations thereof. This list of food products is merely illustrative and not exclusive of the various food products which may be added to the aerated cleanser.

These as well as other features of the present invention will become more apparent upon reference to the drawings as well as described in the Detailed Description of the Invention.

BRIEF DESCRIPTION OF THE DRAWINGS

An illustrative and presently preferred embodiment of the invention is shown in the accompanying drawings in which:

FIG. 1 is a perspective view of the cleanser or the present invention packaged within a personal sized container and lid, and including a dispensing spoon;

FIG. 2 is a top plan view of the cleanser packaged within the personal sized container;

FIG. 3 is a front cross sectional view of a personal sized container with three scoops of cleanser topped with a whipped cleanser;

FIG. 5 is a side view of an aerated cleanser(s) being scooped with an ice cream scoop combined with a food product and corresponding colorants and fragrances;

FIG. 6 is a side view of two different aerated cleansers fabricated with different colorants and fragrances in a hopper and fennel with the cleansers being extruded through the funnel;

DETAILED DESCRIPTION OF THE INVENTION

Figure 4:
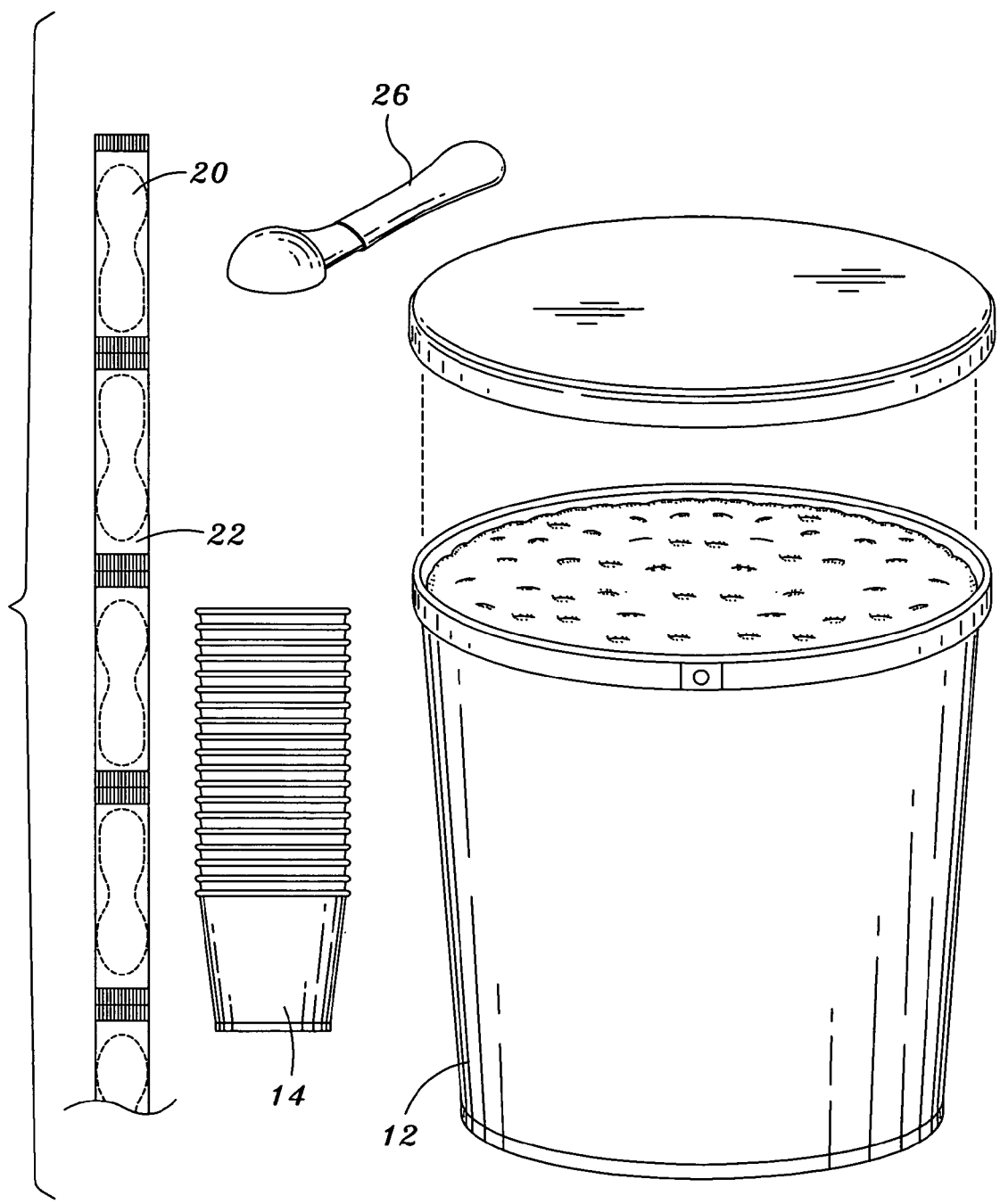
FIG. 4 is a perspective view of a cleanser packaged in a five gallon container with an ice cream scoop, personal sized container and personal sized dispensing spoon attached end to end.

FIGS. 1–9 referenced herein are for the purpose of illustrating the preferred embodiments of the present invention and not to limit the same. For example, as shown in FIG. 1, the present invention, which generally relates to a cleanser 10, is dispensed in an twelve ounce container 12. But, the container 12 in which the cleanser 10 may be dispensed or contained may be of other sizes and/or configurations such as a one and/or five gallon container 12, as will be further discussed below.

The cleanser 10 of the present invention may preferably comprise Glycerin, Water, Sodium Cocoyl Isethionate, Sorbitol, Propylene Glycol, Disodium Lauryl Sulfosuccinate, Stearic Acid, Sodium Chloride, Pentasodium Pentate, Tetrasodium Etidronate. This listing of cleanser ingredients is a glycerin based detergent/cleanser, but the cleanser may comprise other ingredients with other base detergents as is used in the trade. These ingredients may be mixed in with each other in the following proportions as follows: Glycerin—about 10% to about 25%; Water—about 10% to about 25%; Sodium Cocoyl Isethionate—about 10% to about 25%; Sorbitol—about 10% to about 25%; Propylene Glycol—about 5% to about 10%; Disodium Lauryl Sulfosuccinate—about 5% to about 10%; Stearic Acid—about 1% to about 5%; Sodium Chloride—about 0.5% to about 1%; Pentasodium Pentate—up to 0.1%, Tetrasodium Etidronate—up to 0.1%. This detergent/cleanser formulation has been found to simulate the texture and consistency of conventional ice cream, sherbet or the like.

Each of the above listed ingredients of the cleanser 10 may be purchased individually and mixed together to have a consistency of ice cream, sherbet or the like with respect to texture. A variety of colorants and fragrances may additionally be mixed into the cleanser 10 such that the cleanser 10 may visually and aromatically resemble various flavors of ice cream.

By way of example and not limitation, the following preferable colorants may be mixed into the cleanser: Red 3 CI#45430, Blue #1 CI#42090, Yellow 5 CI#11380, Yellow 6 CI#11390, Blue #2 CI#73015, Red 40 CI#16035, or combinations thereof. These as well as other colorants may be mixed into the cleanser 10 to make the cleanser 10 resemble various ice cream flavors such as chocolate, vanilla, chocolate chip, Pralines 'n Cream, or cookies and cream. This list of ice cream and/or sherbet flavors are not the only flavors but are only examples of the numerous possible ice cream flavors that may be visually simulated by the addition of the colorants.

As stated above, the cleanser 10 may have fragrances mixed together with the cleanser 10 such that the cleanser 10 may further resemble ice cream. In particular, by way of example and not limitation, the fragrances may be vanilla, chocolate, grape and other fragrances conventionally used in the trade. This list of fragrances are not the only fragrances that may be added to the cleanser 10 to make the cleanser 10 resemble ice cream and/or sherbet but are merely examples of the numerous possible fragrances that may be mixed into the cleanser 10 to make the cleanser 10 further resemble ice cream.

The detergent/cleanser 10 may be dispensed in various size containers 12 for the purposes of shipping and display to consumers. By way of example and not limitation, the container sizes comprises conventional ice cream containers such as half pint, one pint, eight ounces, twelve ounces, sixteen ounces, half gallon, one gallon, and five gallon containers 12. In this regard, the various sized container 12 may contain or otherwise package the cleanser 10 such that the cleanser 10 may be dispensed for various uses. For example, the smaller sized containers 12 such as the eight ounce container 12 may be utilized by consumers when traveling, and in this regard, the eight ounce container 12 may be regarded as a personal-sized container 12 or a travel-sized container 12. The one and/or five gallon container 12 may be located in stores such that the cleanser 10 may be scooped out into smaller personal-sized containers 12 which further simulate conventional ice cream and are more suitable for consumers.

More particular, the container 12 may have a similar appearance to ice cream containers 12 used in the trade. These contemporary styled ice cream containers 12 may be used to package the cleanser 10 but alternatively, the containers 12 may be a retro-styled ice cream container 12. For example, the container 12 may be circular with a tapered bottom, as shown in FIG. 1. Ridges may be formed vertically about the circumference of the container 12. The container 12 may have a matching circular lid 16 which may be rigidly secured to the inner circumference at the top of the container 12, as shown in FIG. 2. A tab 18 may be formed at an outer edge of the lid 16 such that it may be pulled to remove the lid 16 from the container 12.

The cleanser 10 is specifically adapted to be sold in retail stores in a manner to simulate the sales of conventional ice cream. In particular, the cleanser 10 may be sold prepackaged in personal-sized containers 12. In this regard, the cleanser 10 may be packaged therein so as to resemble a single, double or triple scoop of ice cream. The triple scoop of cleanser 10 is shown in FIG. 3. A personal sized dispensing spoon 20 (see FIG. 1) may be sold with the personal-sized container 12. The spoon which may be a figure eight wooden spoon 20 may be wrapped in paper or plastic wrapping 22. The wrapping 22 may be connected to each other end-to-end in an accordion style manner, as shown in FIG. 4. The dispensing spoon 20 may be sized and configured to fit within a consumer's hand so that the consumer may spoon out a desired amount of cleanser 10 out of the personal-sized container 12 onto the consumer's hand.

In the alternative, the cleanser 10 may be sold by weight or by volume at the retail stores. For example, the cleanser 10 may be sold to retail stores in industrial sized containers 12 such as five gallon containers. A conventional ice cream scoop 26 may then be utilized to dispense the cleanser from the large container 12 to a smaller, personalized container. For example, a plurality of cleansers 10 simulating different ice cream flavors may be provided in five gallon buckets and placed in carts that resemble conventional refrigerated carts. The consumer may select and purchase desired cleansers 10 and the ice cream scoop 26 may be utilized to scoop out a desired amount of cleanser 10 of each ice cream flavor from the industrial sized container 12 and place the same into the personal-sized container 12 or cup. Additionally, the dispensing spoon 20 may be provided for use with the personal-sized container 12. The dispensing spoon 20 may be attached to each other end-to-end in an accordion style, as shown in FIG. 4, so that the consumer may detach one spoon for later use.

The applicants have discovered that the cleanser 10 may be mechanically agitated to aerate the same. By way of example and not limitation, the cleanser 10 is preferably mechanically agitated with a conventional mixer such as a blender. In this regard, this agitation increases the volume of the cleanser 10 compared to the volume of a cleanser 10 which is not agitated to resemble a foamed food product such as whipped cream or the like. The cleanser 10 may be agitated until the same includes about 20% to about 75% air. Preferably, the cleanser 10 is agitated until the cleanser is aerated with about 30% to about 50% air which renders the whipped cleanser to have a consistency similar to conventional dairy whipped cream.

The agitated cleanser 10 may further have colorants and fragrances mixed therein to make the agitated cleanser 10 further resemble whipped cream with respect to its visual appearance and odor. These colorants and fragrances may be the same colorants and fragrances added to the cleanser 10 to make the same resemble ice cream, as discussed above. Moreover, the types of colorants and fragrances that may be mixed into the agitated cleanser 10 is not limited by the expressed colorants and fragrances listed above, but other colorants and fragrances may be mixed into the agitated cleanser 10 to resemble other types of whipped products.

The agitated cleanser 10 having a consistency of whipped cream may also have mixed therein a granulated food product. In particular, the agitated cleanser 10 may preferably be mixed with a granulated sugar, and in this regard, this mixture may be used as a natural exfoliant during the cleansing process. The granulated food product such as granulated sugar may preferably be mixed into the agitated cleanser 10 in the amount of about 10% to about 50% of the cleanser or modified cleanser by volume.

As discussed above, the cleanser 10 may be formed to resemble ice cream and various ice cream flavors. Additionally, the cleanser 10 may be formed to resemble whipped cream and other various ice cream toppings. In this regard, ice cream resembling cleanser 10 may be dispensed in conjunction with the whipped cream resembling cleanser 10 such that the combination may resemble a sundae. Further, the whipped cream resembling cleanser 10 may be sold along side the ice cream resembling cleanser 10 at retail stores such that the consumer may select desired flavors and fragrances of whipped cream resembling cleanser 10 to match the selected flavors of ice cream resembling cleansers 10. In particular, the consumer may scoop out or have sales personnel scoop out selected cleansers 10 resembling ice cream of various ice cream flavors and top it with selected cleanser 10 resembling whipped cream so as to form a sundae. In the alternative, the ice cream resembling cleanser 10 may be sold separately from the whipped cream resembling cleanser 10.

In another embodiment of the present invention, the aerated cleanser 10 (see FIG. 5) may be combined with selective colorants and fragrances to fabricate an aesthetically pleasing glycerin based mixture which is additionally an effective cleanser. The fragrances that may be combined with the aerated cleanser 10 may be lemon, fruit, strawberry, mint, and vanilla. These listed fragrances are merely illustrative of the various types of fragrances the aerated cleanser 10 made be combined with and is not exclusive of the various types of fragrances which the aerated cleanser may be combined with. Selective colorants may be combined with the aerated cleanser 10 which corresponds to the fragrance to be combined with the aerated cleanser. By way of example and not limitation, the colorants may be yellow, orange, red, and green. As an example, red colorant may be combined with the aerated cleanser along with strawberry fragrance. In sum, the agitation of the glycerin based mixture and addition of selective fragrances and colorants produces an aerated cleanser which is extremely aesthetically pleasing and simultaneously effective as a cleanser.

Moreover, the aerated cleanser has been found to be formable into scoops of ice cream. (see FIG. 5) In this regard, the aerated cleanser may have selective fragrances and colorants combined therewith to correspond to various ice cream flavors. This combination of aerated cleanser, fragrance, and colorants may be filled in a bucket 12 and subsequently scooped with an ice cream scoop 26 (see FIG. 5). The scooped aerated cleanser resembles a scoop of ice cream and maintains its shape even at room temperature. As a result, with the addition of appropriate colorants and fragrances, the aerated cleanser 10 alone may be sold to customers in a manner that appears aesthetically to be ice cream but is functionally a cleanser.

Prior to scooping the aerated cleanser 10, a granulated food product 28 (see FIG. 5) such as granulated sugar may be added such that the aerated cleanser 10 may function as a natural exfoliant as well as a cleanser. Subsequently, the aerated cleanser 10 combined with granulated food products 28 may be scooped with the ice cream scoop 26 such that the aerated cleanser 10 may resemble scooped ice cream and simultaneously function as a cleanser and a natural exfoliant.

The aerated cleanser 10 may be contained and sold in a one or five gallon container 12 to be later scooped out by the customer or the sales person at the point of purchase. The aerated cleanser 10 may be sold to the customer in bulk in the one or five gallon container 12. In the alternative, at the point of purchase, the customer or salesperson may scoop out a desired amount of aerated cleanser 10 into a smaller container such as a ½ pint container 12 and sold to the customer. In this regard, the scooped aerated cleanser may resemble ice cream. Moreover, the aerated cleanser 10 may be sold along with an ice cream scoop 26 such that the customer may scoop out the aerated cleanser 10 at home into their bathroom soap dish as desired.

Figure 7:
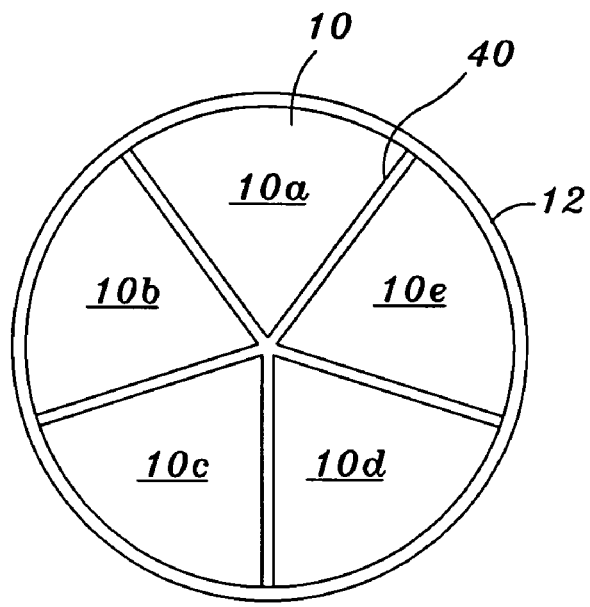
FIG. 7 is a top view of a container wherein aerated cleansers are fabricated with five different colorant and fragrance schemes segregated with dividers.
Figure 8:
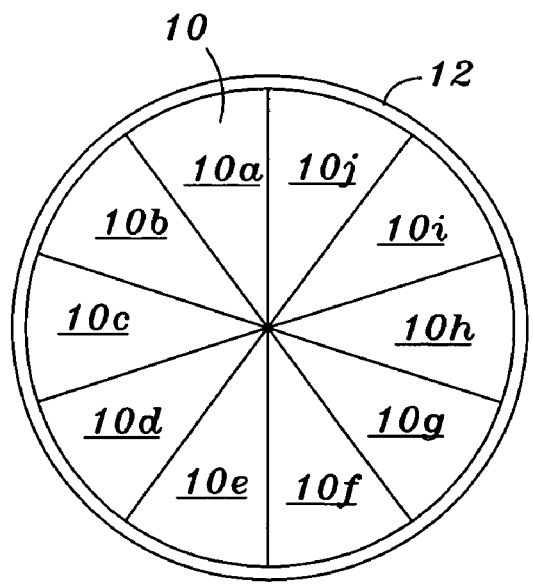
FIG. 8 is a top view of a container with aerated cleanser fabricated with ten different colorant and fragrance schemes placed in the container in a rotating wheel configuration.

The aerated cleanser 10 described above may be combined with various colors and fragrances such that there are a plurality of aerated cleansers 10 with each aerated cleanser 10 having a corresponding fragrance and colorant. For example, a first aerated cleanser 10 may be combined with strawberry fragrance along with red colorant, and a second aerated cleanser 10 may be combined with lemon fragrance along with yellow colorant. Moreover, third, fourth and fifth as well as additional aerated cleansers may have selective fragrances and colorants added thereto to resemble various foods, ice creams and other food products. In this regard, the aerated cleansers may be sold to customers in a single container 12 (see FIGS. 7 and 8). FIG. 7 illustrates five different aerated cleansers 10a, b, c, d, e having five different colorant and fragrance schemes which are divided by dividers 40. And, FIG. 8 illustrates ten different aerated cleansers 10a, b, c, d, e, f, g, h, i having ten different colorant and fragrance schemes. Both FIGS. 7 and 8 illustrate that the aerated cleansers 10 may be arranged in the container 12 in a rotating wheel configuration.

The plurality of aerated cleansers 10 may be filled into a hopper 30 (see FIG. 6). FIG. 6 shows two aerated cleansers 10a, 10b, each fabricated with different colorant and fragrance schemes. The hopper 30 shown in FIG. 6 is merely illustrative of an aspect of the present invention and is not meant as a limitation of the present invention. For example, the hopper 30 shown in FIG. 6 has two different aerated cleansers 10a, b with each aerated cleanser 10 fabricated with a different colorant and fragrance; however, the hopper 30 may be configured to have more than two aerated cleansers 10. The plurality of aerated cleansers 10 may be placed in the hopper 30 with each aerated cleanser 10 in different areas of the hopper 30. The hopper 30 may be connected to a funnel 32 and the aerated cleansers 10a and 10b in the hopper 30 may be squeezed or forced through the fennel 32. Upon proceeding through the funnel 32, the aerated cleansers 10a, 10b do not mix together in a homogeneous fashion but rather, the aerated cleanser 10a remains segregated from adjacent aerated cleanser 10b.

The aerated cleansers 10a, 10b may be squeezed through the funnel 32 by pressurizing the hopper 10 and actuating a measuring piston 34 (see FIG. 6) which may be connected to the funnel 32. The measuring piston 34 opens and closes the exit 36 (see FIG. 6) of the funnel 32 so as to allow or disable the aerated cleansers 10 from flowing therethrough. After the aerated cleansers 10 has been forced through the funnel 32 then the aerated cleanser 32 may fill a one or five gallon container 12 or other container and subsequently sold to a customer.

Moreover, the aerated cleansers 10 forced through the funnel may further have a swirl configuration once the aerated cleansers 10 are filled into the container 12. The swirl configuration is obtained by slowing turning (e.g., staggered or continuous) the container 12 as the aerated cleansers 10a, 10b are filling the container 12. For example, the aerated cleansers 10 may partially fill the container 12 and subsequently, the container 12 may be rotated about its vertical axis 45 degrees. The container 12 may further be filled with the aerated cleansers 10 and subsequently, the container 12 may further be rotated 45 degrees about its vertical axis. In this regard, the aerated cleansers 10 filled in the container may have a swirl configuration. This aerated cleanser 10 with the swirl configuration may also be scooped out with an ice cream scoop 26 such that the same may form scooped ice cream as discussed above.

In yet another embodiment of the present invention, the aerated cleanser 10 may be combined with food products 38 such as real fruits and/or vegetables (see FIG. 5). The aerated cleanser 10 may be combined with the fruits and/or vegetables 38 in all of the various cleanser forms discussed above. The various fruits, vegetables and food products 38 may include berries, apples, oranges, cabbage, and raisins. These examples of various fruit, vegetables and food products 38 are merely illustrative of the wide array of fruit, vegetables, and fruit products 38 that may be added and combined with the aerated cleanser 10 and are not an exclusive list of fruits, vegetables, and food products 38 that may be combined with the aerated cleanser 10.

As stated above, the cleanser 10 may be agitated by placing the same 10 in a mixer such as a blender until a desired degree of aeration has been accomplished. With regard to the fruit products 38 identified above, the same 38 may be combined with the aerated cleanser 10 prior to the cleanser 10 being agitated or during agitation of the cleanser 10, or after the cleanser 10 has been agitated. The food products 38 when added or combined with the aerated cleanser 10 may have already been chopped or minced to a desired particle size before it is combined with the cleanser 10 regardless of whether it has been agitated. If the cleanser 10 is agitated with a blender then the particulate size of the fruit product may further be reduced during agitation or blending of the cleanser 10 by combining the food product 32 to the cleanser 10 during or before agitation.

The combination of cleanser 10 and food product 32 may be sold to prospective customers of cleansers 10 with respect to a particular motif. The motif may be an ice cream parlor such as Baskin Robbins or the motif may be a juice bar such as Jamba Juice. These motifs are merely examples of the various motifs by which the combination of cleanser 10 and food product 38 may be sold and are not exclusive of all possible motifs by which the combination of cleanser 10 and food product 38 may be sold. In this detailed description, the ice cream motif has been selected to merely illustrate this aspect of the present invention and is not meant to limit the present invention. For example, a retail store may be stocked with a plurality of aerated cleansers 10 along with a plurality of real food products 38 such as those identified above. The plurality of aerated cleansers 10 may be placed within a mock ice cream refrigerator, and the plurality of real food products 38 may be placed in a working refrigerator depending on whether the real food products requires refrigeration. In both respects, the refrigerators may have a glass top such that prospective customers may view the same.

Prospective customers may enter the retail store with the aim of purchasing customized combinations of cleansers 10 and food products 38. For example, at the retail store, the prospective customer may enter the retail store and request a sales person to combine a selected aerated cleaner 10 resembling an ice cream flavor and at least one selected food product 38. The sales person may combine the selected cleanser 10 and food products 38 and return the same to the prospective customer in an ice cream container 12 or in the form of scoop(s) of ice cream in an appropriate container 12. The combination of the aerated cleanser 10 and the fruit product 38 may be presented in the configurations discussed above such as rotating wheel configuration or swirl configuration.

The various aspects of the present invention in relation to the aerated cleanser 10 may be applied to the non-aerated cleanser 10, and conversely, the various aspects of the present invention in relation to the cleanser 10 may be applied to the aerated cleanser 10.

This description of the various embodiments of the present invention is presented to illustrate the preferred embodiments of the present invention, and other inventive concepts may be otherwise variously embodied and employed. The appended claims are intended to be construed to include such variations except insofar as limited by the prior art.

What is claimed is:

1. A method of forming swirl configuration in an aerated cleanser, the method comprising the steps of:
   a. providing at least two glycerin based mixtures, each mixture having about 20% to about 75% air, each mixture resembling a different food product;
   b. filling a hopper with the mixtures adjacent to each other; and
   c. extruding the mixtures from the filled hopper through a funnel into a container wherein the cleanser comprises a mixture of about 10% to about 25% glycerin, about 10% to about 25% water, about 10% to 25% sodium cocoyl isethionate, about 10% to 25% sorbitol, about 5% to about 10% propylene glycol, about 5% stearic acid, about 0.5% to about 1% sodium chloride and pentasodium pentate.

2. The method of claim 1 further comprising the step of rotating the extruded mixtures in the container to form swirls.

3. A method of dispensing cleansers, the method comprising:
   a. providing a variety of glycerin based mixtures resembling a plurality of food products;
   b. providing a plurality of food products;
   c. combining a selected food product with a selected glycerin based mixture; and
   d. combining selected food product and selected glycerin based mixture until the combination has about 20% to about 75% air wherein said cleanser comprises a mixture of about 10% to about 25% glycerin, about 10% to about 25% water, about 10% to 25% sodium cocoyl isethionate, about 10% to 25% sorbitol, about 5% to about 10% propylene glycol, about 5% stearic acid, about 0.5% to about 1% sodium chloride and pentasodium pentate.

4. The method of claim 3 wherein the food product is selected from the group consisting of fruit, vegetable, berries, and combinations thereof.

5. The method of claim 3 wherein the combination food product and mixture is blended until the combination has about 30% to about 50% air.

6. The method of claim 3 further comprising the steps of:
   a. placing the mixtures in a mock ice cream refrigerator; and
   b. placing the food product in a working ice cream refrigerator.

7. The method of claim 6 wherein the refrigerators are placed in a retail store having a motif of a juice bar.

8. A method of fabricating a cleanser, the method comprising the steps of:
   a. aerating a first glycerin based mixture to have about 20% to about 75% air;
   b. adding a first colorant to the first glycerin based mixture; and
   c. adding a first fragrance to the first glycerin based mixture wherein said cleanser comprises a mixture of about 10% to about 25% glycerin, about 10% to about 25% water, about 10% to 25% sodium cocoyl isethionate, about 10% to 25% sorbitol, about 5% to about 10% propylene glycol, about 5% stearic acid, about 0.5% to about 1% sodium chloride and pentasodium pentate.

9. The method of claim 8 further comprising the steps of:
   d. aerating a second glycerin based mixture to have about 20% to about 75% air;
   e. adding a second colorant to the second glycerin based mixture; and
   f. adding a second fragrance to the first glycerin based mixture.

10. The method of claim 9 further comprising the step of:
   g. placing the aerated first mixture with first colorant and first fragrance added thereto adjacent to the aerated second mixture with second colorant and second fragrance added thereto.

* * * * *